United States Patent [19]

Jacobs et al.

[11] Patent Number: 4,465,892

[45] Date of Patent: Aug. 14, 1984

[54] ISOMERIZATION OF PARAFFINS OR OLEFINS WITH BRIDGED CLAYS

[76] Inventors: Pierre Jacobs, 6, Populieren Straat, 1686 Goik; Georges Poncelet, 15, rue de Wavre, 5998 Beauvechain; Alain Schutz, 4, rue Godincourt, 6778 Musson, all of Belgium

[21] Appl. No.: 538,085

[22] Filed: Oct. 3, 1983

Related U.S. Application Data

[62] Division of Ser. No. 411,769, Aug. 26, 1982.

[30] Foreign Application Priority Data

Aug. 27, 1981 [FR] France ................................ 81 16387

[51] Int. Cl.$^3$ ........................... C07C 5/13; C07C 5/22
[52] U.S. Cl. .................................... 585/666; 585/752; 585/670; 585/739

[58] Field of Search ................ 208/120; 585/648, 651, 585/739, 752, 666, 670

[56] References Cited

U.S. PATENT DOCUMENTS

| | | | |
|---|---|---|---|
| 3,655,798 | 4/1972 | Csicsery et al. | 585/666 |
| 3,892,655 | 7/1975 | Hickson | 208/120 |
| 3,959,118 | 5/1976 | Granquist | 208/120 |
| 3,976,598 | 8/1976 | Daviditz | 423/328 |
| 4,078,991 | 3/1978 | Goldstein | 208/120 |
| 4,176,090 | 11/1979 | Vaughan et al. | 423/328 |

*Primary Examiner*—Delbert E. Gantz
*Assistant Examiner*—Lance Johnson
*Attorney, Agent, or Firm*—Curtis, Morris & Safford

[57] ABSTRACT

A process for isomerization of paraffinic or olefinic hydrocarbons using as catalysts or as supports for catalysts bridged clays which are prepared by an aqueous clay suspension subjected to a dialysis.

14 Claims, 5 Drawing Figures

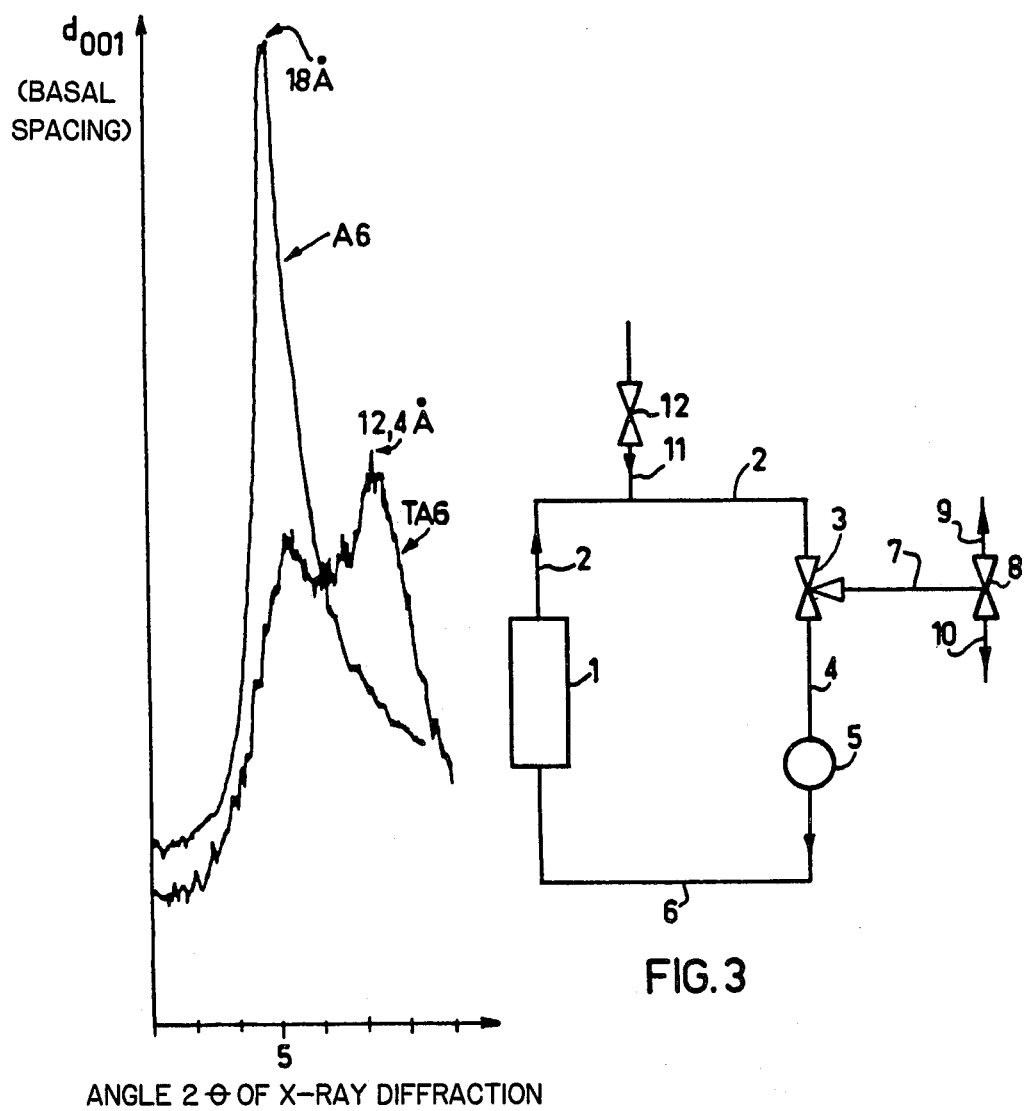

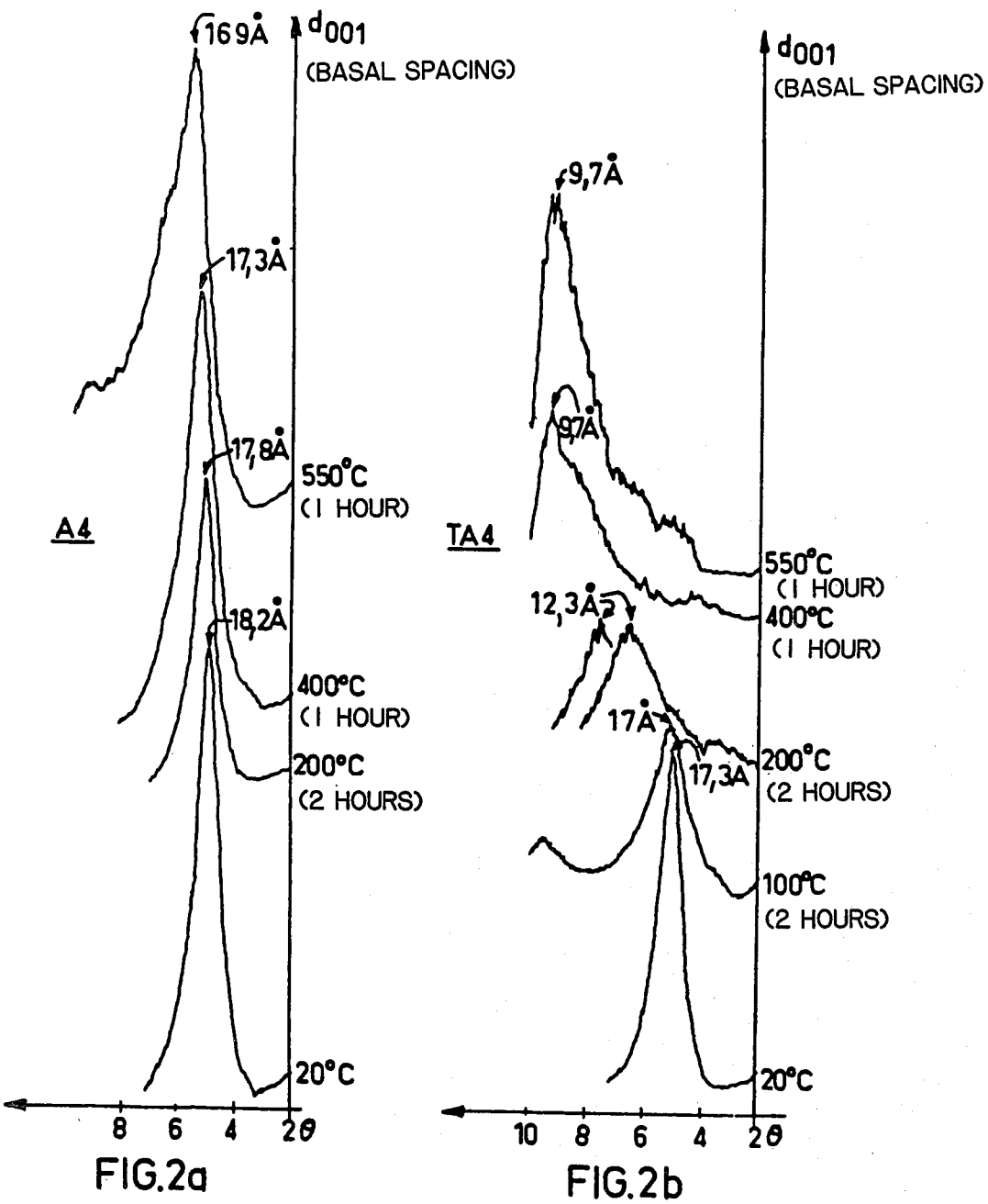

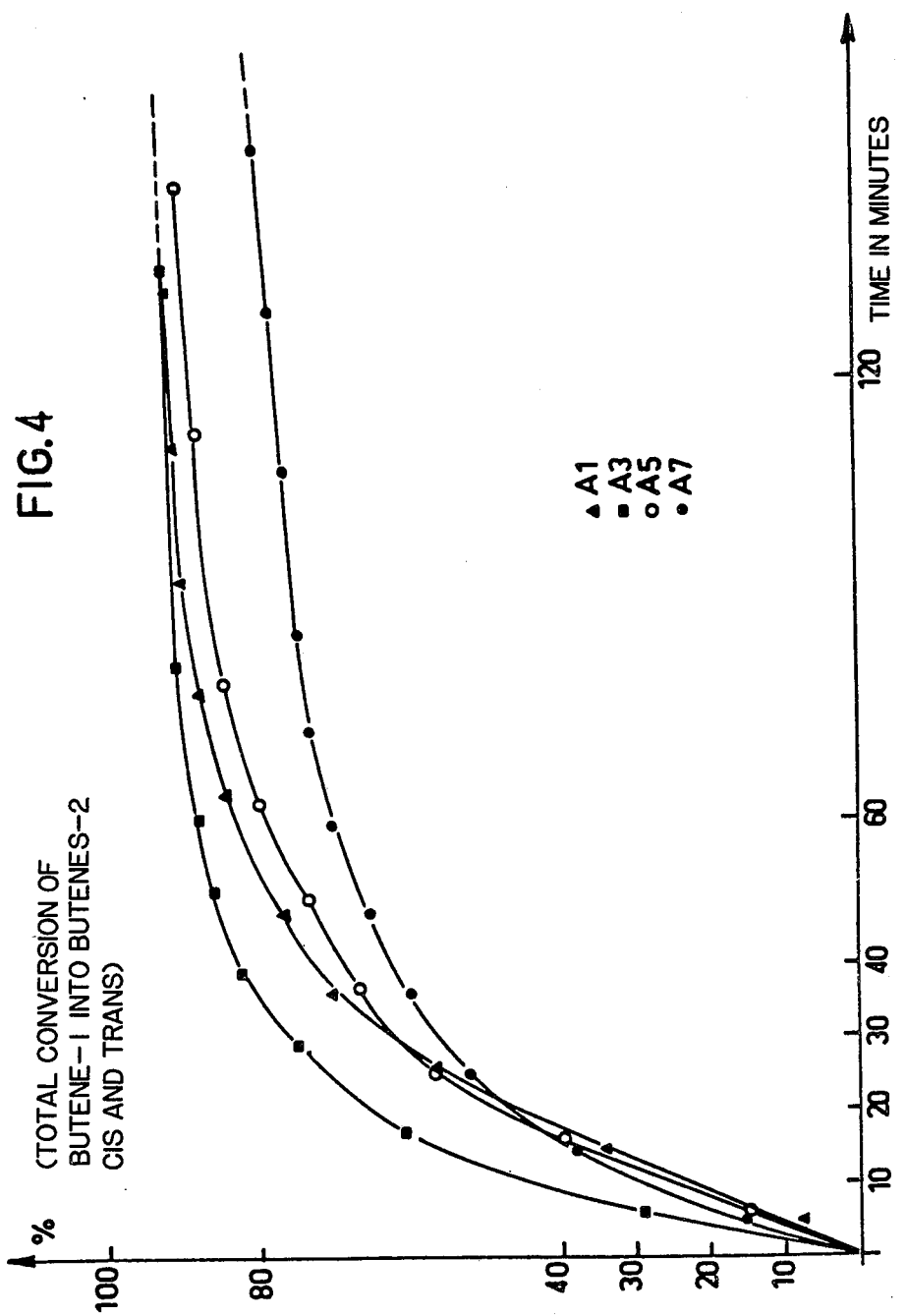

ISOMERIZATION OF PARAFFINS OR OLEFINS WITH BRIDGED CLAYS

This application is a division of application Ser. No. 411,769, filed Aug. 26, 1982.

The present invention relates to a process for the preparation of bridged clays, clays prepared by said process, and uses for said clays.

Some clays have an expandable network structure. They have the property of being able to adsorb especially water between the individual sheets of which they are made up. This is true especially of the montmorillonite group of clays. These clays have a structure which may be defined, in a simplified manner, as a three-layer structure comprising two single layers of $SiO_4$ tetrahedrons and a dioctahedral or trioctahedral intermediate layer. Cohesion between the layers is assured by the fact that the apical oxygen atoms are coordinated. The silicon atoms of the tetrahedrons may be partly replaced by aluminum atoms.

Similarly, in the octahedrons of the $AlX_6 (X=O, OH)$ intermediate layer, the aluminum atoms may be partly replaced by magnesium or iron atoms. Iron-bearing montmorillonites, called nontronites, are known in which the octahedral layer is formed entirely of iron octahedrons, the charge of the sheet being the result of substitutions at the level of the tetrahedral layers. Saponite, a trioctahedral clay (magnesium octahedral layer), has a charge due to substitutions at the level of the silicic tetrahedral layers.

It is well known that the specific surface of a support is a very important factor in catalysis, and because of their property of being expandable, these clays might be used as catalysts or supports for catalysts, especially for the conversion of hydrocarbons. However, once expanded, in other words, after having adsorbed water between their individual sheets, these clays have the drawback of losing their expanded character when heated to 100° C., and consequently of not retaining the increase in specific surface which may result from their expansion.

It should be noted that the state of expansion of a clay is defined by the intersheet spacing and the basal spacing, which are measured by x-ray diffraction.

As its name implies, the intersheet spacing is the spacing between two sheets. In the unexpanded state of the dried clay, it is zero.

The basal spacing, represented by the symbol $d_{001}$, is defined as the sum of the thickness of a sheet and the intersheet spacing.

In the case of montmorillonite, the thickness of a sheet is 9.6 angstrom units. In the expended state, the intersheet spacing may exceed about 10 angstrom units, and the basal spacing may therefore exceed about 20 angstrom units.

With a view to using expanding clays as catalyst supports or as catalysts, it has been sought to obtain clays having a maximum basal spacing that can be maintained when the clay is subjected to a heat treatment.

Thus it has been found that pillars or bridges can be inserted between the clay sheets to obtain clays which hereinafter will be referred to as "bridged clays".

One well-known method consists in introducing between the clay sheets bridges formed by oligomers of a metal hydroxide, and in particular of an aluminum hydroxide.

This method, described specifically in an article by Lahav, U. Shani and J. Shabtai which appeared in Clays and Clay Minerals, volume 26 (1978), No. 2, pages 107 to 115, consists in contacting an oligomer of aluminum hydroxide with an aqueous suspension of montmorillonite. The method described makes it possible to obtain a basal spacing of about 18 angstrom units. The article points out that the hydroxyaluminum solution obtained by reaction of soda with aluminum chloride must be aged before it is brought into contact with the clay suspension. This process therefore is rather time-consuming. Moreover, the concentration of the clay suspensions used is very low. It ranges from 50 to 200 mg per liter of suspension, equivalent to from 0.005 to 0.02 weight percent. This method therefore makes it necessary to handle large volumes of suspension, which of course is a disadvantage.

The article further points out that it is preferable to use a relatively high $OH^-/Al^{3+}$ ratio, namely, 2.33. Now when an $OH^-/Al^{3+}$ ratio on the order of 3 is used, there is the risk of uncontrolled crystallization of bayerite and/or gibbsite, $Al(OH)_3$, outside the sheets, which is an additional disadvantage.

The method described in that article thus is afflicted with several drawbacks.

Another method, described in French Pat. No. 2,394,324, consists in contacting clay with a solution of aluminum chlorohydroxide called "chlorhydrol". This method likewise entails drawbacks since clay and "chlorhydrol" must be brought into contact with each other at a relatively high temperature (the patent mentions temperatures on the order of 70° C.), and aging is likewise required.

The invention proposes a new method of preparing "bridged clays" which is not afflicted with the drawbacks of the prior art outlined above.

To this end, the invention disclosed herein is a process for the preparation of bridged clays which is characterized in that a mixture of an aqueous solution of at least one metal hydroxide and an aqueous clay suspension is subjected to dialysis.

Aqueous solution of at least one metal hydroxide means a solution containing $OH^-$ and $M^x$ ions of at least one metal in which the $OH^-/M^x$ ratio is such that the precipitation threshold of the hydroxide is not reached.

In accordance with the invention, the hydroxide may be selected from the group comprising the hydroxides of the elements of groups IIB, IIIB, IVB, VB, VIB, VIIB, VIII, IA, IIA, IIIA, IVA, VA and VIA, Vb and VIb of the periodic table of the elements.

In the process in accordance with the invention, the hydroxide may be obtained by the action of a base on a metal-salt solution in which the metal is present as a cation, or of an acid on a metal-salt solution in which the metal is present as an anion.

The mixture of the solution of at least one hydroxide of a metal and the clay suspension may be produced in different ways, namely:

by preparing the hydroxide solution, for example, by the action of a base on a salt, and then adding the solution so obtained to the clay suspension;

by adding to the clay suspension a solution of the metal salt and then adding a base solution; or by adding to the clay suspension simultaneously a solution of the metal salt and a base.

In other words, the hydroxide solution may be prepared before it is mixed with the clay suspension, or by adding the precursors of the hydroxide solution to the clay suspension.

The hydroxide solution may also be obtained from certain compounds which hydrolyze spontaneously, without it being necessary to add a base; for example, from the oxychlorides of zirconium, vanadium, molybdenum or rhenium.

One of the important parameters in the process of the invention is the $OH^-/M^x$ ion ratio in the hydroxide solution, wherein x defines the degree of oxidation of the metal.

When x=I, the $OH^-/M^I$ ratio may range from 0.2 to 1, and preferably from 0.2 to 0.8, and more particularly from 0.3 to 0.7.

When x=II, the $OH^-/M^{II}$ ratio may range from 0.2 to 2, and preferably from 0.4 to 1.8, and more particularly from 0.5 to 1.4.

When x=III, the $OH^-/M^{III}$ ratio may range from 0.3 to 3, and preferably from 0.6 to 2.4, and more particularly from 0.8 to 1.8.

When x=IV, the $OH^-/M^{IV}$ ratio may range from 0.4 to 4, and preferably from 0.8 to 3.6, and more particularly from 1 to 2.8.

In the process of the invention, the concentration in the mixture of the clay suspension and the hydroxide solution of the ion of the metal used to form the metal-oxide pillars should be sufficiently high to result in the formation of metal-oxide pillars yet not so high that too much metal oxide is inserted between the clay sheets, which would impair the porosity of the clay.

Said concentration, expressed in milliequivalents (meq) of the ion of the metal involved per gram of clay, may range from 6 to 60, and preferably from 10 to 30.

The clay concentration in the final mixture, that is to say, after mixing of the hydroxide solution and the initial clay suspension, should be sufficiently high to obviate the handling of large volumes of mixture, yet not excessively high since too high a clay concentration in the mixture would make the latter difficult to handle.

The clay concentration in the final mixture may range from 0.1 to 4 weight percent, and preferably from 0.8 to 1.5 weight percent, for example.

The clays which may be used in the process of the invention may be selected from the group formed by the swelling clays (smectites, whether natural or produced by hydrothermal synthesis).

The final step of the process in accordance with the invention consists in subjecting the mixture of the solution of at least one metal hydroxide and the clay suspension to dialysis.

The dialysis may be carried out by placing said mixture in a container formed by a semipermeable membrane selected from the group comprising the membranes based on regenerated cellulose, or by any other semipermeable membrane.

The container is then immersed in water, preferably demineralized water although any kind of water (distilled water, tap water, etc.) may be used as its ionic strength will be lower than that of the water contained in the dialysis membrane.

The operation may be carried out discontinuously or continuously. In the latter case, the container is placed in a stream of water.

The dialysis operation may be carried out at ambient temperature but can be accelerated by raising the temperature of the water. The temperature is limited by the boiling temperature of the water at the pressure at which the operation is performed.

The clays prepared by the process in accordance with the invention possess very good thermal stability and preserve their basal spacing when they are brought to a high temperature. They are therefore suitable for use as catalyst supports and as catalysts, particularly in the conversion of hydrocarbons.

They are especially well suited for use as catalysts or catalyst supports in the isomerization of paraffinic or olefinic hydrocarbons or in the cracking of these hydrocarbons, optionally in the presence of hydrogen.

Thus at least one of the elements from groups IB, IIB, IIIB, IVB, VB, VIB, VIIB, VIII, IA, IIA, IIIA, IVA, VA and VIIA of the periodic table of the elements may be deposited on these clays.

The six examples which follow will serve to illustrate the invention without limiting it.

The six figures which accompany the present specification are explained in these examples.

FIGS. 1, 2a and 2b are x-ray diffraction charts of control clays and of clays prepared according to this invention.

FIG. 3 schematically illustrates apparatus used for testing the clays prepared according to this invention.

FIG. 4 is a chromatography chart showing the isomerization activity of clays prepared according to this invention.

EXAMPLE 1

This example relates to the preparation of bridged clays A1, A2, A3, A4, A5, A6, A7, A8, A9, A10, A11, A12, A13 and A14 by the process of the invention as well as of control bridged clays TA2, TA4 and TA6 by an allied process which did not, however, include the final dialysis operation.

The starting material was a montmorillonite, which was saturated with sodium ions, $Na^+$, by being treated repeatedly with a normal aqueous solution of sodium chloride.

The excess sodium chloride was eliminated by centrifugation. The clay was washed several times with demineralized water, centrifugation being effected after every wash.

The fraction whose particle size was 2 microns or less was separated by decantation, the fraction of a particle size above 2 microns being eliminated.

From said clay fraction, aqueous suspensions S1 and S2 containing 2.5 and 4.16 weight percent clay, respectively, were prepared.

There were further prepared:

An aqueous solution I of aluminum chloride. $AlCl_3.6H_2O$;

an aqueous solution II of chromium chloride, $CrCl_3.6H_2O$; and an aqueous solution III of sodium hydroxide, NaOH.

The three solutions I, II and III had a molar concentration of 0.2.

Solution III was added to solution I and/or to solution II in varying amounts gradually, with continuous agitation, so as to avoid the formation or appearance of turbidity. In this way, different hydroxide solutions of varying $OH^-/Al^{3+}$ or $OH^-/Cr^{3+}$ or $OH^-/Cr^{3+}$ plus $Al^{3+}$ ratios were obtained.

The different hydroxide solutions obtained were then mixed in varying amounts, with agitation, with a certain amount of suspension S1 or S2.

In this way, mixtures containing the metal or metals in varying concentrations were obtained.

For preparation of the control clays TA2, TA4 and TA6, some of the mixtures obtained were simply washed with demineralized water.

For the preparation of clays by the process of the invention, the mixtures obtained were placed in a pocket formed of a semipermeable cellulose membrane having an average porosity of 24 angstrom units, marketed under the trademark VISKING by Medicell International Ltd.

The pocket was placed in 10 liters of demineralized water for a period of 24 hours. The operation was repeated four times.

Following this dialysis operation, samples were taken from the products obtained by the two procedures, and these samples were examined by x-ray diffraction.

The suspensions were centrifuged, and the various products obtained were dried by lyophilization.

The conditions of preparation of the bridged clays obtained and their basal spacing, measured by x-ray diffraction, are given in Table 1 which follows.

It is apparent from Table 1 that the basal spacing of the clays prepared by the process of the invention is greater than that of the clays prepared by a process without dialysis. Comparison of the clays A6 and TA6 will bring this out particularly well.

The x-ray diffraction spectrum of the clays A6 and TA6, dried at ambient temperature, is given in the accompanying FIG. 1.

It will be noted that the basal spacing of clay A6 is greater than that of clay TA6 and that the line of clay A6 is narrower and more intense than that of clay TA6. This indicates that the aluminum hydroxy layer interposed between the sheets is very much better organized in clay A6 than in clay TA6.

The clays so prepared were then subjected to different heat treatments. After each treatment their basal spacing was measured. The results before and after the heat treatment are presented in Table 2 which follows.

TABLE 1

| Clay prepared | Amount of solution or suspension used in the preparation of the clay (in milliliters) | | | | | $OH^-/M^{3+}$ iron ratio (6) | Concentration in meq, per gram of clay (7) | Mole percent $Cr^{3+}$ / $Cr^{3+}$ plus $Al^{3+}$ (8) | Basal spacing (9) |
|---|---|---|---|---|---|---|---|---|---|
| | Solution I (1) | Solution II (2) | Solution III (3) | Clay suspension $S_1$ (4) | Clay suspension $S_2$ (5) | | | | |
| A1 | 333 | 0 | 266 | 400 | 0 | 0.8 | 20 | — | 19 |
| A2 | 333 | 0 | 333 | 400 | 0 | 1.0 | 20 | — | 19 |
| TA2 | 333 | 0 | 333 | 400 | 0 | 1.0 | 20 | — | 16.2 |
| A3 | 333 | 0 | 400 | 400 | 0 | 1.2 | 20 | — | 19 |
| TA3 | 333 | 0 | 400 | 400 | 0 | 1.2 | 20 | — | 16.2 |
| A4 | 333 | 0 | 466 | 400 | 0 | 1.4 | 20 | — | 18.2 |
| TA4 | 333 | 0 | 466 | 400 | 0 | 1.4 | 20 | — | 17.3 |
| A5 | 333 | 0 | 533 | 400 | 0 | 1.6 | 20 | — | 19.1 |
| A6 | 333 | 0 | 566 | 400 | 0 | 1.7 | 20 | — | 18 |
| TA6 | 333 | 0 | 566 | 400 | 0 | 1.7 | 20 | — | 12.4 |
| A7 | 333 | 0 | 666 | 400 | 0 | 2.0 | 20 | — | 19.5 |
| A8 | 166.5 | 0 | 333 | 0 | 240 | 2.0 | 10 | — | 18 |
| A9 | 166.5 | 0 | 383 | 0 | 240 | 2.3 | 10 | — | 17.9 |
| A10 | 166.5 | 0 | 416 | 0 | 240 | 2.5 | 10 | — | 17.9 |
| A11 | 0 | 333 | 466 | 400 | 0 | 1.4 | 20 | — | 17.6 |
| A12 | 0 | 333 | 666 | 400 | 0 | 2.0 | 20 | — | 19 |
| A13 | 230 | 100 | 333 | 400 | 0 | 1.0 | 20 | 30 | 17.6 |
| A14 | 165 | 165 | 333 | 400 | 0 | 1.0 | 20 | 50 | 17.2 |

(1) Solution of $AlCl_3 \cdot 6H_2O$, 0.2 molar.
(2) Solution of $CrCl_3 \cdot 6H_2O$, 0.2 molar.
(3) Solution of NaOH, 0.2 molar.
(4) Suspension, 2.5 weight percent.
(5) Suspension, 4.16 weight percent.
(6) In the metal hydroxide solution (in the case of a mixed Al and Cr solution).
(7) Concentration of the metal ion or ions (in the case of a mixed Al and Cr solution) in the mixture of hydroxide solution and clay suspension.
(8) In the case of a mixed Al and Cr solution.
(9) After drying at ambient temperature.

TABLE 2

| Clay | Basal spacing in angstrom units | | | | | | |
|---|---|---|---|---|---|---|---|
| | Before heat treatment | Heat-treating conditions | | | | | |
| | | 2 hours at 100° C. | 2 hours at 200° C. | 1 hour at 300° C. | 1 hour at 400° C. | 1 hour at 500° C. | 1 hour at 550° C. |
| A1 | 19 | | | 18.1 | | 17.1 | |
| A2 | 19 | | | 18.1 | | 17.1 | |
| TA2 | 16.2 | | | 11.2 | | 9.7 | |
| A3 | 19 | | | 18 | | 17 | |
| TA3 | 16.2 | | | 11.2 | | 9.4 | |
| A4 | 18.2 | | 17.8 | | 17.3 | | 16.9 |
| TA4 | 17.3 | 17 | 12.3 | | 9.7 | | 9.7 |
| A5 | 19.1 | | | 17.6 | | 16.3 | |
| A6 | 18 | | | | | | |
| TA6 | 12.4 | | | | | | |
| A7 | 19.5 | | | 17 | | 16 | |
| A8 | 18 | | | 17.3 | | 16.9 | |
| A9 | 17.9 | | | 17.3 | | 16.8 | |
| A10 | 17.9 | | | 17.2 | | 16.3 | |
| A11 | 17.6 | | | 16.4 | | | |

TABLE 2-continued

| | Basal spacing in angstrom units | | | | | | |
|---|---|---|---|---|---|---|---|
| | Before | Heat-treating conditions | | | | | |
| Clay | heat treatment | 2 hours at 100° C. | 2 hours at 200° C. | 1 hour at 300° C. | 1 hour at 400° C. | 1 hour at 500° C. | 1 hour at 550° C. |
| A12 | 19 | 18 | | 17 | | | |
| A13 | 17.6 | | | 14.7 | | | |
| A14 | 17.2 | | | 14.5 | | | |

As may be seen from Table 2, the basal spacing of of the clays prepared by the process of the invention is reduced but slightly with temperature, which of course is an advantage when these clays are used as catalyst supports or as catalysts.

This is not the case with the control clays prepared by a process without dialysis.

Shown in FIGS. 2a and 2b by way of example are the peaks obtained by x-ray diffraction for the clays A4 and TA4, respectively, from which it is apparent that the basal spacing of clay TA4 is reduced by heat treatment.

The specific surfaces of the various bridged clays were measured on the basis of nitrogren adsorption isotherms obtained at the temperature of liquid nitrogen by the BET method. The specific surfaces ranged from 200 to 400 m²/g. The clays had first been degassed under vacuum at 300° C. for 16 hours.

The porosity distribution determined on the basis of nitrogen desorption isotherms was binodal, with pores ranging in diameter from 40 to 50 angstrom units and pores of a diameter between 10 and 20 angstrom units.

EXAMPLE 2

This example relates to the preparation of a bridged clay B by the process in accordance with the invention.

The starting material was a montmorillonite, which was treated as in Example 1, that is to say, exchange by means of sodium chloride, then separation of the fraction whose particle size was 2 microns or less.

To an aqueous suspension of this montmorillonite containing 2.5 weight percent of the clay there was added 30 milliliters of an 0.2 molar solution of zirconium oxychloride, $ZrOCl_2$. 130 milliliters of distilled water was then added to give an aqueous suspension containing 0.5 weight percent of clay.

The suspension was dialyzed by means of a membrane identical to that used in Example 1 at the rate of 1 liter of demineralized water per gram of clay.

The dialysis water was replaced after 24 hours. A sample was taken after each dialysis for examination by x-ray diffraction.

The samples were dried at ambient temperature, then subjected to different heat treatments.

The results before and after heat treatment are presented in Table 3 which follows.

TABLE 3

| | Basal spacing in angstrom units | | | |
|---|---|---|---|---|
| Treatment | After 1 dialysis | After 3 dialyses | After 4 dialyses | After 5 dialyses |
| Drying at ambient temperature | 11.3 | 19.6 | 18.5 | 19 |
| At 110° C. | 11 | 16.4 | 16.1 | 16.4 |
| At 400° C. | 10 | 15.7 | 15.7 | 15.7 |

The influence of the dialysis is clearly apparent from this table. The basal spacing remains fairly high despite the heat treatment.

EXAMPLE 3

This example relates to the preparation of a bridged clay C by the process of the invention and of a control bridged clay TC by a process which does not include a final dialysis step.

The starting material was a montmorillonite fraction identical to that used in Examples 1 and 2.

To an aqueous suspension of this montmorillonite, titanium sulfate, $Ti(SO_4)_2$, in an acidic solution was added at the rate of 33 mg of titanium per gram of clay.

The final concentration of the clay suspension was 0.25 weight percent. A sample was taken and dried. This was the control clay TC.

The suspension was dialyzed as in Example 2 and samples were taken, treated and examined in the same manner.

The results are presented in Table 4 which follows.

TABLE 4

| | Basal spacing in angstrom units | | | |
|---|---|---|---|---|
| | Control clay TC | Clay C after | | |
| Treatment | (without dialysis) | one dialysis | two dialyses | three dialyses |
| Drying at ambient temperature | 12.2 | 12.4 | 23.2 | 23 |
| At 110° C. | Not measured | 12.1 | 20 | 23.2 |
| At 300° C. | Not measured | Not measured | Not measured | 23.8 |

The influence of dialysis is clearly apparent from this table. The basal spacing remains fairly high despite the heat treatment.

EXAMPLE 4

This example relates to the preparation of a bridged clay D by the process of the invention and of a control bridged clay TD by a process which does not include a final dialysis step.

The starting material was a montmorillonite fraction identical to that used in Examples 1, 2 and 3.

To an aqueous suspension of this montmorillonite containing 2.5 weight percent of the clay, 20 meq of holmium per gram of clay was added in the form of holmium nitrate, $Ho(NO_3)_3.6H_2O$, in aqueous solution.

The final suspension contained 1 weight percent of clay.

The suspension was dialyzed as in Example 3 and samples were taken, treated and examined in the same manner. The x-ray diffraction pattern showed that the 001 lines becomes finer with the number of dialyses and increases in intensity, which manifests the beneficial effect of dialysis on the regular arrangement of the sheets, which itself is due to the provision of the bridges.

Shown in table V which follows are the intensities of the 001 line at 15.5 angstrom units as a function of the number of dialyses.

The intensities were measured on the basis of the x-ray diffraction pattern and multiplied by the number of shots per second.

TABLE 5

| | Intensity of 001 line multiplied by the number of shots/sec | | | |
|---|---|---|---|---|
| | Control clay TD | Clay D after | | |
| Treatment | (without dialysis) | one dialysis | two dialyses | three dialyses |
| Drying at ambient temperature | 1,220 | 7,500 | 11,000 | 10,000 |
| At 110° C. | 680 | 2,680 | 2,800 | Not measured |
| At 300° C. | 120 | 1,120 | 1,640 | 3,000 |

The influence of dialysis is clearly apparent from this table and persists despite the heat treatment.

EXAMPLE 5

This example relates to the hydroisomerization and hydrocracking of a charge of normal decane with the aid of catalysts prepared from the clays of Example 1.

From the various clays of Example 1, catalysts containing 1 weight percent platinum were prepared by impregnating the clays with an aqueous solution of tetramineplatinum chloride, $Pt(NH_3)_4Cl_2$.

After being dried at 110° C. for 16 hours, the products obtained were calcined in air and then reduced by a hydrogen stream.

Catalysts which are referenced in Table 6 which follows were so obtained.

TABLE 6

| Starting clay | Catalyst |
|---|---|
| A2 | C2 |
| A3 | C3 |
| A4 | C4 |
| A7 | C7 |
| A8 | C8 |
| A9 | C9 |
| A10 | C10 |
| A11 | C11 |
| A13 | C13 |
| A14 | C14 |

A normal-decane hydroisomerization and hydrocracking test was then run with each catalyst by placing a given amount of catalyst in a 5-ml reactor. A mixture of normal decane and hydrogen was then passed over the catalyst at atmospheric pressure and at such normal-decane feed rate $F_o$ at the top of the reactor that, with W representing the catalyst weight, the $W/F_o$ ratio was 518 kg/second/mole, the hydrogen/normal decane ratio being 71 standard liters per liter.

The tests were run with the temperature being increased from 100° to 300° C. to secure total conversion of the normal decane.

Successive checks were made, through gas-chromatographic analyses of the gases leaving the reactor, to determine:

the temperature at which 20% conversion of normal decane was obtained;

the temperature at which the isomerization maximum was reached; and the temperature at which 20% cracking was secured.

The amounts of catalyst used and the results of these tests are presented in Table 7 which follows.

TABLE 7

| Test No. | Catalyst | Catalyst pretreating conditions. Oxidation and calcination temperatures in °C. | Amount of catalyst Weight mg | Amount of catalyst Volume ml | Temperature at which 20% conversion was obtained °C. | Isomerization maximum % | Isomerization maximum Temp. °C. | Temperature at which 20% cracking was secured, °C. |
|---|---|---|---|---|---|---|---|---|
| 1 | C2 | 400 | 160 | 0.6 | 195 | 52 | 245 | 245 |
| 2 | C3 | 400 | 200 | 0.5 | 190 | 55 | 232 | 231 |
| 3 | C4 | 400 | 130 | 0.6 | 197 | 65 | 249 | 269 |
| 4 | C7 | 400 | 85 | 0.5 | 200 | 55 | 252 | 230 |
| 5 | C8 | 400 | 125 | 0.6 | 205 | 55 | 255 | 275 |
| 6 | C9 | 400 | 200 | 0.5 | 231 | 50 | 281 | 330 |
| 7 | C10 | 400 | 190 | 0.5 | 208 | 55 | 262 | 272 |
| 8 | C11 | 400 | 186 | 0.6 | 192 | 58 | 227 | 227 |
| 9 | C13 | 300 | 420 | 0.6 | 167 | 50 | 190 | 190 |
| 10 | C14 | 300 | 420 | 0.6 | 147 | 55 | 172 | 172 |
| 11 | C14 | 420 | 390 | 0.6 | 180 | 55 | 220 | 220 |

As may be seen from Table 7, the bridged clays prepared by the process of the invention can be used to produce isomerization and cracking catalysts which are efficient at relatively low temperatures.

These reactions will not occur when an unbridged clay containing 1 weight percent platinum is used.

EXAMPLE 6

This example relates to the isomerization of a charge of butene-1 with the aid of clays A1, A3, A5 and A7.

The apparatus diagrammed in FIG. 3 was used to carry out these tests.

Into a 25-ml reactor 1, 140 mg clay was placed. The reactor was connected through a line 2 to a three-way valve 3, which in turn was connected through a line 4 to a circulating pump 5, which in turn was connected to the reactor 1 through a line 6.

The reactor 1 and the lines 2, 4 and 6 thus formed a loop whose total volume was 1.3 liters and in which it was possible to:

produce a vacuum by means of a line 7, a three-way valve 8 and a line 9 connected to a vacuum pump (not shown);

take gas samples for analysis through line 7, the three-way valve 8 and a line 10 connected to a chromatograph (not shown); and introduce a gas such as butene-1 through a line 11 provided with a valve 12 and and connected to line 2.

The reactor was equipped with a heating system (not shown).

The tests were run in the following manner: After the clay had been placed in the reactor, the loop was degassed by means of the vacuum pump 5, the reactor temperature being 250° C. When the pressure reached $10^{-6}$ mm Hg, the vacuum circuit was isolated and the reactor temperature was reduced to 100° C.

Butene-1 was then introduced into the loop in such an amount that the pressure was 40 mm Hg.

The circulating pump 5 was cut in and samples were periodically taken and analyzed by chromatography.

The results obtained are shown in FIG. 4.

It is apparent from FIG. 4 that the clays prepared by the process in accordance with the invention have very good isomerizing activity.

We claim:

1. In the isomerization of hydrocarbons chosen from the group consisting of paraffins and olefins, the improvement comprising the use at a temperature ranging from 100° C. to 300° C. of a catalyst which comprises an element from group VIII of the periodic table of the elements and a bridged clay prepared by the process comprising subjecting a mixture of an aqueous solution of at least one metal hydroxide and an aqueous clay suspension to dialysis.

2. A process according to claim 1, wherein said conversion catalyst contains platinum.

3. A process according to claim 1, wherein the dialysis is carried out with the aid of a semipermeable membrane selected from the group consisting of organic membranes.

4. A process according to claim 3, wherein said membrane is selected from the group consisting of membranes based on regenerated cellulose.

5. A process according to claim 4, wherein said catalyst contains platinum.

6. A process according to claim 1, further cracking simultaneously isomerizing and cracking said hydrocarbons in the presence of hydrogen.

7. A process according to claim 6, wherein said catalyst contains platinum.

8. A process according to claim 6, wherein said hydroxide is selected from the group formed by the hydroxides of the elements of groups IIB, IIIB, IVB, VB, VIB, VIIB, VIIIB, IA, IIA, IIIA, IVA, VA and VIA of the periodic table of the elements and said hydroxide is capable of forming an aqueous solution, the clay is a natural or synthetic smectite swelling clay, the concentration of the metal ion of the hydroxide in the mixture of clay suspension and hydroxide solution, expressed in milliequivalents per gram of clay, ranges from 6 to 60, and the concentration of clay in the mixture of clay suspension and hydroxide solution ranges from 0.1 to 4 weight percent.

9. A process according to claim 8, wherein the degree of oxidation of the metal M of the hydroxide is equal to I and the $OH^-/M^I$ ratio ranges from 0.2 to 1.

10. A process according to claim 9, wherein the degree of oxidation of the metal M of the hydroxide is equal to II and the $OH^-/M^{II}$ ratio ranges from 0.2 to 2.

11. A process according to claim 8, wherein the degree of oxidation of the metal M of the hydroxide is equal to III and the $OH^-/M^{III}$ ratio ranges from 0.3 to 3.

12. A process according to claim 11, wherein the metal of the hydroxide is at least one metal selected from the group formed by aluminum, chromium and holmium.

13. A process according to claim 8, wherein the degree of oxidation of the metal M of the hydroxide is equal to IV and the $OH^-/M^{IV}$ ratio ranges from 0.4 to 4.

14. A process according to claim 13, wherein the metal of the hydroxide is at least one metal selected from the group formed by zirconium and titanium.

* * * * *

UNITED STATES PATENT AND TRADEMARK OFFICE
CERTIFICATE OF CORRECTION

PATENT NO. : 4,465,892

DATED : Aug. 14, 1984

INVENTOR(S) : Pierre Jacobs, et al.

It is certified that error appears in the above-identified patent and that said Letters Patent is hereby corrected as shown below:

Column 12, line 1, (claim 6, line 1) after "further" delete "cracking" and insert --comprising--.

Signed and Sealed this

Eighth Day of January 1985

[SEAL]

Attest:

GERALD J. MOSSINGHOFF

*Attesting Officer*  Commissioner of Patents and Trademarks